US008765181B2

(12) United States Patent
Liang et al.

(10) Patent No.: US 8,765,181 B2
(45) Date of Patent: Jul. 1, 2014

(54) NANO ANTICANCER MICELLES OF VINCA ALKALOIDS ENTRAPPED IN POLYETHYLENE GLYCOLYLATED PHOSPHOLIPIDS

(75) Inventors: Wei Liang, Beijing (CN); Min'an Lou, Beijing (CN); Wei Si, Beijing (CN)

(73) Assignee: Beijing Diacrid Medical Technology Co., Ltd, Beijing (CN)

( * ) Notice: Subject to any disclaimer, the term of this patent is extended or adjusted under 35 U.S.C. 154(b) by 1567 days.

(21) Appl. No.: 12/066,066

(22) PCT Filed: Sep. 8, 2006

(86) PCT No.: PCT/CN2006/002327
§ 371 (c)(1),
(2), (4) Date: Sep. 9, 2008

(87) PCT Pub. No.: WO2007/028341
PCT Pub. Date: Mar. 15, 2007

(65) Prior Publication Data
US 2009/0053293 A1      Feb. 26, 2009

(30) Foreign Application Priority Data

Sep. 9, 2005   (CN) ........................... 2005 1 0098381
Sep. 6, 2006   (CN) ........................... 2005 1 0112888

(51) Int. Cl.
*A61K 9/19*      (2006.01)
(52) U.S. Cl.
USPC ......................................... 424/489; 514/937
(58) Field of Classification Search
CPC ........ A61K 9/19; A61K 9/0019; A61K 9/127
USPC .................. 424/489, 450; 514/937
See application file for complete search history.

(56) References Cited

U.S. PATENT DOCUMENTS

2004/0228911 A1*  11/2004  Zhang et al. ................... 424/450
2005/0003008 A1*   1/2005  Rapoport ....................... 424/486
(Continued)

FOREIGN PATENT DOCUMENTS

CN         1429120 A     7/2003
CN         1739525 A     3/2006
(Continued)

OTHER PUBLICATIONS

Lukyanov et al Journal of Controlled Release, vol. 91, pp. 97-102, 2003.*
Lukyanov et al Advanced Drug Delivery Reviews, vol. 56, pp. 1273-1289, 2004.*
(Continued)

*Primary Examiner* — Gollamudi Kishore
(74) *Attorney, Agent, or Firm* — Knobbe, Martens, Olson & Bear, LLP

(57) ABSTRACT

The present invention provides a nano-micellar preparation containing vinca alkaloids antitumor agent for intravenous injection, which cincludes a therapeutically effective amount of vinca alkaloids antitumor agent (vinblastine, vincristine, vindesine and vinorelbine), a phosphatide derivatized with polyethylene glycol, together with pharmaceutically acceptable adjuvants. The preparation is prepared by encapsulating the medicament with a nano-micelle to obtain the nano-micellar preparation containing vinca alkaloids antitumor agent for injection. The vinca alkaloids antitumor agent and the phosphatide derivatized with polyethylene glycol form a nano-micelle with a highly uniform particle size. In the micelle, the hydrophobic core of encapsulated medicament is surrounded by polyethylene glycol molecules to form a hydrophilic protective layer, so that the medicament is prevented from contacting with the enzymes and other protein molecules in blood and being recognized and phagocytozed by reticuloendothelial system in body, and the circulation time in vivo of the micelle is prolonged.

8 Claims, 3 Drawing Sheets

(56) References Cited

U.S. PATENT DOCUMENTS

2005/0053668 A1    3/2005  Vail
2006/0057219 A1*   3/2006  Nagasaki et al. ............. 424/490
2006/0216342 A1*   9/2006  Torchilin et al. ............. 424/450

FOREIGN PATENT DOCUMENTS

WO         00/62813    * 10/2000
WO    WO 01/87345 A1    11/2001

OTHER PUBLICATIONS

Lukyanov, A.N. et al. 2004 "Micelles from lipid derivatives of water-soluble polymers as delivery system for poorly soluble drugs" *Advanced Drug Delivery Reviews* 56: 1273-1289.

Lukyanov, A.N. et al. 2003 "Micelles from polyethylene glycol/phosphatidylethanolamine conjugates for tumor drug delivery," *Journal of Controlled Release* 91: 97-102.

Torchilin, V.P. et al. 2001 "Structure and design of polymeric surfactant-based drug delivery systems" *J Control Release* 73:137-172.

* cited by examiner

NANO ANTICANCER MICELLES OF VINCA ALKALOIDS ENTRAPPED IN POLYETHYLENE GLYCOLYATED PHOSPHOLIPIDS

RELATED APPLICATIONS

This application is a U.S. National Phase of International Application No. PCT/CN2006/002327, filed Sep. 8, 2006, designating the U.S. and published not in English as WO 2007/028341 on Mar. 15, 2007, which claims the benefit of Chinese application No. 200510098381.2, filed Sep. 9, 2005 and Chinese application No. 200610112888.3, filed Sep. 6, 2006.

FIELD OF THE INVENTION

The present invention relates to a nano-micellar preparation containing vinca alkaloids antitumor agent for intravenous injection and method for producing thereof.

BACKGROUND OF THE INVENTION

Vinca alkaloids antitumor agent is a class of effective broad-spectrum antitumor agent, which is important and widely used in the clinic treatment of various cancers, such as leukaemia, lymphoma, breast cancer, lung cancer, liver cancer and many other solid tumors. This class of antitumor agents mainly includes vinblastine (VLB), vincristine (VCR), vindesine (VDS) and vinorelbine (VNR). Similar to other cytotoxic antineoplastics, these antitumor agents, however, lack selectivity for tumor tissues and lead to a severe dose-dependent acute toxicity, which is represented clinically as nausea, emesis, alopecia, and blood vessel irritation. More severe are the inhibition of bone marrow and strong neurotoxicity, and repeated administration will lead to severe complications. The toxic side effect of vinca alkaloids antitumor agent greatly limits their clinic application in the long-term treatment for tumors.

One approach to significantly decrease toxicity of vinca alkaloids antitumor agent is to alter their tissue distribution and improve their selectivity for tumor tissues. The liposome preparation of vinca alkaloids antitumor agent could reduce the toxic side effect of the agent and increase their distribution in tumor tissues, so as to mitigate their dose-dependent acute toxicity. The liposome preparation has been approved for the clinic treatment of various types of cancer and a satisfying therapeutical effect has been achieved. Two liposomal products, amphotericin liposome and paclitaxel liposome, have been approved by China State Drug Administration. The liposome preparations of vinca alkaloids antitumor agent, however, also suffer from many disadvantages. For example, the medicament is encapsulated in inner water phase and released from the liposome quickly, which results in instability of the preparation. The minimal size of the liposome is 50 nm and the entry of the liposome into cells is completed via fusion and pinocytosis mechanisms. Thus, the cytotoxic effect of the medicament encapsulated in liposome is weaker than that of free medicament. The production process of the liposome is complicated and the complexing of several lipid components (at least two lipid components) is required, wherein special equipments and devices are required to control the particle size. In addition, flocculation occurs frequently during the storage.

In water, amphiphilic molecules will aggregate spontaneously to form micelle when the concentration of the molecules is beyond critical micelle concentration. Taking advantage of this property, medicament is encapsulated in the hydrophobic core of the micelle. Micellar preparations have been used in clinic treatment practice for a long time. For example, deoxycholate sodium was utilized to solubilize amphotericin B and the like. A paper titled with "polymer micelle: a novel drug carrier" by Kun etc., summarized the use of micelle as a drug carrier (Adv. Drug. Del. Rev., 21:107-116, 1976). Recently, as a targeting, long-circulating and sustained release drug carrier, polymer micelle has been paid a great attention and becomes a research focus in the drug delivery systems. Yokoyama et al employed polymers to encapsulate antitumor drug and investigated its activity against solid tumor and cytotoxicity as well as its long-circulating property in blood, wherein the polymers was capable of forming micelle (Cancer res. 51: 3229-3236(1991)). Lipids modified with PEG-phospholipid have been demonstrated to be characterized by their long circulation in animal and human body, and can be safely used in clinic treatment (Gregoriadis, G. TIBTECH, 13: 527-537, 1995). As a carrier for drugs with poor solubility, polyethylene glycol-phospholipid micelle has been comprehensively summarized by investigators (Torchilin, V. P. J. controlled Release, 73:137-172).

Polyethylene glycol (PEG) is a water-soluble polymer that is stable under physiological condition. Because the space structure of PEG is capable of preventing the approach of plasma proteins, PEG has been widely used to modify the properties of phospholipid and protein drugs. In nanoparticle delivery system, PEG is capable of forming a hydrophilic protection layer on the surface of particles to prevent the aggregation of the particles, avoiding being recognized and phagocytized by reticuloendothelial system in body, and extending the retention time of drugs in blood circulation, whereby a long circulation is achieved.

Nano-micelle prepared from a phospholipid derivatized with polyethylene glycol possesses advantages over other nanoparticles. Its size is small between 10 nm and 30 nm. The nano-micelle is a dynamically stable system, which avoids the disadvantage of other nanoparticle delivery system, i.e. easy to aggregate, and on the other hand reaches lesion sites more easily, whereby the drug distribution in the tumor tissue is increased.

SUMMARY OF THE INVENTION

One objective of the present invention is to provide a nano-micellar preparation containing vinca alkaloids antitumor agent for intravenous injection, which is a dynamically stable system, has good stability and can be used in targeted therapy in vivo. Thus, the nano-micellar preparation is capable of improving the drug distribution in tumor tissues, increasing effectiveness and decreasing toxicity.

Another objective of the present invention is to provide a method that producing the nano-micellar preparation containing vinca alkaloids antitumor agent for intravenous injection.

The present invention provides a nano-micellar preparation containing vinca alkaloids antitumor agent for intravenous injection, comprising a therapeutically effective amount of vinca alkaloids antitumor agent, a phosphatide derivatized with polyethylene glycol, together with pharmaceutically acceptable adjuvants.

In one embodiment, a nano-micellar preparation containing vinca alkaloids antitumor agent is provided, which is produced by a suitable preparation method from basic adjuvant, a phosphatide derivatized with PEG.

DETAILED DESCRIPTION OF THE INVENTION

The present invention provides a nano-micellar preparation containing vinca alkaloids antitumor agent for intravenous injection, which comprises vinca alkaloids antitumor agent, a phosphatide derivatized with polyethylene glycol, together with pharmaceutically acceptable adjuvants.

According to the present invention, the vinca alkaloids antitumor agent is one or more medicaments selected from the group consisted of vinblastine (VLB), vincristine (VCR), vindesine (VDS) and vinorelbine (VNR).

In the present invention, the molar ratios of the vinca alkaloids antitumor agent and the phosphatide derivatized with polyethylene glycol are ranged from 1:0.5 to 1:10, and preferably from 1:2 to 1:5 for vinblastine (VLB), vincristine (VCR) and vindesine (VDS), and preferably from 1:4 to 1:6 for vinorelbine (VNR).

In one embodiment, the phosphatide derivatized with polyethylene glycol is formed by coupling polyethylene glycol molecule to an active group on the phospholipid molecule through a covalent bond, wherein the active group is a nitrogenous base or hydroxyl group.

In another embodiment, the phosphatide according to present invention is a phosphatide derivatized with polyethylene glycol, wherein the fatty acid in the phosphatide part composed of 10 to 24 carbon atoms, preferably 12, 14, 16, 18, 20, 22 or 24 carbon atoms. The fatty acid chain may be saturated or partially saturated. In particular, the fatty acid may be lauric acid (C12), myristic acid (C14), palmitic acid (C16), stearic acid or oleic acid or linoleic acid (C18), arachidic acid (C20), behenic acid (C22) or lignocerate (C24).

In still another embodiment, the phosphatide part may be phosphatidylethanolamine (PE), phosphatidylcholine (PC), phosphatidylinositol (PI), phosphatidylserine (PS), diphosphatidyl glycerol, acetal phosphatide, lysophosphatidylcholine (LPC), or lysophosphatidyl ethanolamine (LPE).

In another aspect, the phosphatide in the phosphatide derivatized with polyethylene glycol is preferably phosphatidylethanolamine, and more particular, distearyl phosphatidylethanolamine, dipalmitoyl phosphatidylethanolamine, dioleoyl phosphatidylethanolamine.

The polyethylene glycol in the phosphatide derivatized with polyethylene glycol has a molecular weight of between 200 and 20000 daltons (correlating with the number of ethoxy group in the long chain of PEG), preferably between 500 and 10000, more preferably between 1000 and 10000 (the number of ethoxy group is 22 to 220), and most preferably 2000.

In a preferred embodiment, the phosphatide derivatized with polyethylene glycol according to present invention is 1,2-distearoyl-sn-glycero-3-phosphoethanolamine-N-[poly(ehtyleneglycol) 2000] (PEG2000-DSPE).

The nano-micellar preparation containing vinca alkaloids antitumor agent according to present invention, as required, may be a solution or in a lyophilized form.

In the nano-micellar preparation containing vinca alkaloids antitumor agent according to present invention, the micelle has a size range of 5-100 nm, preferably 10-50 nm, most preferably 10-20 nm. The concentrations of the vinca alkaloids antitumor agent ranged from 1 to 10 mg per ml in the preparation, preferably from 1 to 4 per ml, more preferably from 1 to 3 mg per ml. The concentrations of the phosphatide derivatized with polyethylene glycol ranged from 1 to 500 mg per ml in the preparation, preferably from 10 to 30 mg per ml in the preparation.

In another aspect, the phosphatide derivatized with polyethylene glycol is formed by coupling polyethylene glycol molecule to the phospholipid molecule through a covalent bond.

The nano-micellar preparation containing vinca alkaloids antitumor agent according to present invention utilizes a phosphatide derivatized with polyethylene glycol alone or in combination with other phosphatides as carrier, wherein a therapeutically effective amount of vinca alkaloids antitumor agent is encapsulated in the formed nanomicelle by a particular preparation process. When necessary, an antioxidant, osmotic pressure adjusting agent, or pH adjusting agent may be added.

In still another aspect, the micellar preparation comprises vinca alkaloids antitumor agent, an amphiphilic molecule and a pharmaceutically acceptable antioxidant, osmotic pressure adjusting agent, or pH adjusting agent. The amphiphilic molecule may be a phosphatide derivatized with polyethylene glycol or other phosphatides. Other phosphatides include phosphatidic acid, phosphatidylinositol, phosphatidylserine, phosphatidyl glycerol, cardiolipin, soyabean lecithin, phosphatidylcholine, phosphatidylethanolamine, hydrolecithin etc.

In the micellar preparation according to present invention, the molar percentage of the phosphatide derivatized with PEG in total phosphatide is in the range of 20% to 100%, preferably 60% to 100%.

The final micellar preparation may be a solution, which comprises 1 mg/ml to 10 mg/ml of vinca alkaloids antitumor agent, 1 mg/ml to 500 mg/ml of total phosphatide. The concentration of other additives is 0.01% to 5%.

The final micellar preparation may be a lyophilized powder, which comprises 0.02% to 50% by weight of vinca alkaloids antitumor agent, 50% to 95% by weight of total phosphatide and 10% to 90% by weight of other additives.

Because both vinca alkaloids antitumor agent and phosphatides are easy to be oxidized, the micellar preparation of vinca alkaloids antitumor agent according to present invention may further comprise an antioxidant, such as water soluble antioxidant (ascorbic acid, sodium bisulphate, EDTA, concentrations: 0.01 to 1.0 wt %) and fat soluble antioxidant (tocopherol, BHA, propyl gallate, concentrations: 0.01 to 1.0 wt %).

As required, pH adjusting agents (various buffer systems, such as citric acid-sodium citrate, acetic acid-sodium acetate, phosphate etc.) may be added to the micellar preparation according to present invention with concentrations of 1 mM to 100 mM. The medicament solution is adjusted to a pH of 3.0 to 8.0, more preferably 6 to 7.5.

As required, an osmotic pressure adjusting agent (sodium chloride, glucose, mannitol) may be added to the micellar preparation according to present invention. The osmotic pressure adjusting agent may be various pharmaceutically acceptable salts and carbohydrates for adjusting osmotic pressure to be isotonic to or somewhat higher than that of human body (the osmotic pressure range of human body is 290-310 mmol/L).

The invention further provides a method that producing the nano-micellar preparation containing vinca alkaloids antitumor agent, comprising: encapsulating the vinca alkaloids antitumor agent in a nanomicelle formed with a phosphatide derivatized with polyethylene glycol so as to prepare the nano-micellar preparation containing vinca alkaloids antitumor agent for intravenous injection.

In one particular embodiment, the method that producing the nano-micellar preparation containing vinca alkaloids antitumor agent according to present invention includes the following steps:

(1) dissolving the vinca alkaloids antitumor agent and the phosphatide derivatized with polyethylene glycol in an organic solvent;

(2) removing the organic solvent so as to obtain a polymer lipid film containing the vinca alkaloids antitumor agent;

(3) adding water or a buffer solution to the polymer lipid film obtained in step (2) and hydrating, so as to obtain the nanomicelle of phosphatide derivatized with polyethylene glycol, the vinca alkaloids antitumor agent being encapsulated therein.

The encapsulation efficiency of the vinca alkaloids antitumor agent in the micelle is at least 90%.

The method of present invention is further characterized by one of the following:

the organic solvent in step (1) is methanol, ethanol, chloroform, DMSO or the mixtures thereof;

the organic solvent is removed under reduced pressure and/or under vacuum condition in step (2);

the buffer solution in step (3) is citrate or phosphate buffer solution; and the hydrating in step (3) is performed in water bath at a temperature between 25° C. and 70° C., preferably between 45° C. and 60° C. for vinblastine (VLB), vincristine (VCR) and vindesine (VDS) for 1 to 2 hours, and at a temperature between 25° C. and 70° C., preferably between 50° C. and 65° C. for vinorelbine (VNR) for 0.5 to 2 hours.

In one embodiment, the method according to present invention further comprises adjusting the pH of the obtained micelle solution to 3.0-8.0, preferably 6-7.5, and more preferably 6.5-7.4, with a pH adjusting agent.

In another embodiment, the method according to present invention further comprises lyophilizing the obtained micelle solution to produce a lyophilized preparation.

In details, the micellar preparation according to present invention is produced by the following procedures: dissolving the vinca alkaloids antitumor agent, the phosphatide derivatized with polyethylene glycol and fat soluble additives in an organic solvent in a leptoclados-type bottle; removed the organic solvent to form a thin uniform lipid film on the surface of the leptoclados-type bottle dryness using a rotary evaporator; dissolving water soluble additives (water soluble antioxidant, osmotic pressure adjusting agent, pH adjusting agent) in water, and then the water solution is added to the leptoclados-type bottle and hydration is performed by shaking; filtering through 0.22 μm microfiltration membrane for filtration sterilization to produce the micellar preparation of vinca alkaloids antitumor agent for intravenous injection. The particle size of the formed nanomicelle is in the range of 10-50 nm, preferably 10-30 nm. As required, the preparation may be a suspension or in a lyophilized form.

For the purpose of better understanding of the invention, several technical terms are defined as follows.

"Micelle" refers to an amphiphilic molecule which is capable of aggregating spontaneously to form micelle when the concentration of the molecules in water solution is beyond critical micelle concentration (CMC). The structure of the micelle differs from that of liposome in that the micelle does not possess a lipid bilayer structure. In general, in the structure of micelle, hydrophobic part orients toward inner to form a hydrophobic core, while hydrophilic part orients toward outside to form a hydrophilic surface. The particle size of micelle is small with average diameters about 10-20 nm. Therefore, micelle is not only a thermodynamically stable system, but also a dynamically stable system. In addition, the micelle particle does not congregate and stratify easily and its loading capability is high, even when the drug concentration is low.

"Phosphatide", the molecular structure of phosphatide is similar to that of fat and differs in that only two fatty acids is linked to the glycerol molecule in phosphatide and the third hydroxyl group is coupled with phosphoric acid to form ester. With such a structure, phosphatide enables itself an amphiphilic molecule, wherein its phosphoric acid or phosphoric acid ester terminus is polar and easy to attract water to constitute a hydrophilic head of the phosphatide molecule, while its fatty acid terminus are hydrophobic, forming a hydrophobic tail of the phosphatide molecule. The main phosphatide involved in the invention is phosphatide derivatized with polyethylene glycol. In present invention, the phosphatide derivatized with polyethylene glycol may also be used in combination with other phosphatides.

"Therapeutically effective amount" refers to the amount of the vinca alkaloids antitumor agent when a therapeutic effect is produced. According to the invention, the unit dosage of vinca alkaloids antitumor agent is 5-100 mg, preferably 10-20 mg, most preferably 20 mg for vinblastine (VLB), vincristine (VCR) and vindesine (VDS), 1-50 mg, preferably 1-20 mg, most preferably 10 mg for vinorelbine (VNR), and can be modified according to individual requirement of each subject.

The nano-micellar preparation containing vinca alkaloids antitumor agent according to present invention utilizes polyethylene glycol (PEG) to prevent the nano-micellar preparation from being phagocytized by reticuloendothelial system in body. Thus, the retention time of the nanomicelle in blood circulation is prolonged and the dynamical property of the drug in body (drug distribution) is improved, so that the effectiveness is increased and toxicity is decreased.

As described above, vinca alkaloids antitumor agents lead to a severe dose-dependent acute toxicity and lack selectivity for tumor tissues. Conventional injection solution of vinca alkaloids antitumor agents, upon being injected into body, results in a severe nerve toxicity. The toxic side effect of vinca alkaloids antitumor agent greatly limits their clinic application in the long-term treatment for tumors. Liposomes of vinca alkaloids antitumor agent, however, suffer from many disadvantages, including leakage from liposomes and poor stability during storage.

To overcome the disadvantages of above preparations, the present invention utilizes a phosphatide derivatized with polyethylene glycol alone or in combination with other phosphatides to produce the micelle preparation containing vinca alkaloids antitumor agent, wherein the encapsulation percentage exceeds 90%. The major technological advantage of present invention is the utilization of phosphatide derivatized with polyethylene glycol, which is capable of spontaneously forming a nanomicelle with a very uniform particle size. The size of the nanomicelle is in a range of 10-30 nm. In the micelle, the hydrophobic core of encapsulated medicament is surrounded by polyethylene glycol molecules to form a hydrophilic protective layer, so that the medicament is prevented from contacting with the enzymes and other protein molecules in blood and being recognized and phagocytized by reticuloendothelial system in body. Thus, the circulation time in vivo of the micelle is prolonged. The encapsulation of the medicament in the hydrophobic core of micelle prevents the medicament from being destroyed by external factors (water, oxygen, light) and improves significantly the stability of the medicament during storage. Furthermore, the micelle is capable of altering the dynamical property of drug (drug distribution) in vivo, increasing the drug distribution in tumor tissues and thereby improving efficacy and decreasing toxicity.

MODE FOR CARRYING OUT THE INVENTION

Figure 1:
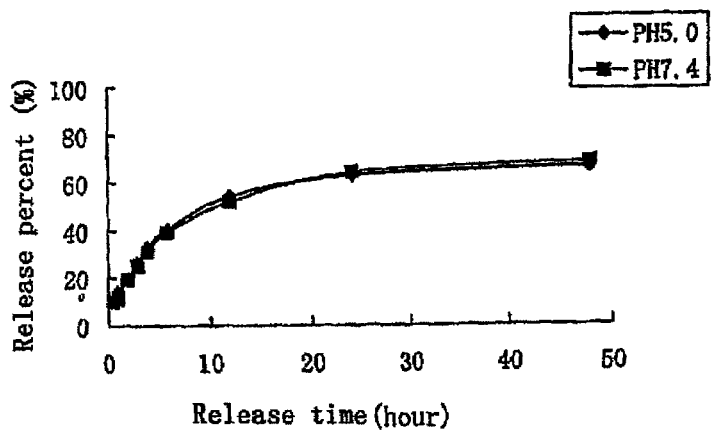
FIG. 1 illustrates the release profiles of VCR encapsulated PEG2000-DSPE micelles.

The following examples are intended to illustrate the invention, but are in no way intended to limit the scope thereof.

Example 1

Production of Nano-Micellar Preparation Containing Vinca Alkaloids Antitumor Agent The formulation of the preparation is listed in Table 1:

TABLE 1

The formulation of the nano-micellar preparation containing vinca alkaloids antitumor agents

| Medicament | Lipids/Medicament (mol/mol) | Medicament (mg/ml) | Hydrated solution |
|---|---|---|---|
| Vinblastine | 2:1 | 2 | Citrate buffer solution, pH 7.0 |
| Vincristine | 2:1 | 2 | Citrate buffer solution, pH 7.0 |
| Vindesine | 2:1 | 2 | Citrate buffer solution, pH 7.0 |
| Vinorelbine | 5:1 | 2 | Water |

Preparation process: vinblastine (VLB), vincristine (VCR), vindesine (VDS) and vinorelbine (VNR) with a ratio according to above formulation were dissolved in ethanol (1-5 mg/ml), respectively. In addition, PEG 2000 distearyl phosphatidylethanolamine (PEG2000-DSPE, purchased from Shanghai Dongshang Company, China) was weighed, dissolved in a suitable amount of chloroform, and then put into a 100 ml leptoclados-type bottle. The organic solvent was removed using a rotary evaporator to form a thin uniform phosphatide film on the surface of the leptoclados-type bottle. A citrate buffer solution, pH 7.0 or distilled water was added to the leptoclados-type bottle and hydration was performed by shaking at 37° C. for 1 hour or at 55° C. for 30 minutes under the protection of nitrogen atmosphere. 0.22 μm microfiltration membrane was used for filtration sterilization to produce the micellar preparation containing vinca alkaloids antitumor agent for intravenous injection. The obtained sample was a clear colorless suspension, and had an average particle size of 15 nm with a size distribution between 10 nm and 20 nm. The encapsulation efficiency was over 90%.

Example 2

The Encapsulation Efficiency of VCR-PEG2000-DSPE Micelles

The formulation of the preparation is listed in Table 2:

TABLE 2

The encapsulation efficiency of VCR -PEG2000-DSPE micelles

| Lipids/Medicament (mol/mol) | Medicament (mg/ml) | Hydrated solution | Encapsulation efficiency (%) |
|---|---|---|---|
| 1:1 | 2 | Citrate buffer solution, pH 7.0 | 91.5 |
| 2:1 | 2 | Citrate buffer solution, pH 7.0 | 94.5 |
| 4:1 | 2 | Citrate buffer solution, pH 7.0 | 96 |
| 6:1 | 2 | Citrate buffer solution, pH 7.0 | 99 |
| 10:1 | 2 | Citrate buffer solution, pH 7.0 | 99.6 |

Preparation process: According to Lipids/Medicament ratios in above formulation, VCR was weighed and dissolved in ethanol (2 mg/ml). PEG2000-DSPE was weighed and dissolved in a suitable amount of chloroform, and then put into a 100 ml leptoclados-type bottle. The organic solvent was removed using a rotary evaporator to form a thin uniform phosphatide film on the surface of the leptoclados-type bottle. A citrate buffer solution, pH 7.0 or water for injection was added to the leptoclados-type bottle and hydration was performed by shaking at 37° C. for 1 hour or at 55° C. for 30 minutes under the protection of nitrogen atmosphere. 0.22 μm microfiltration membrane was used for filtration sterilization to produce the micellar preparation of vincristine for intravenous injection. The obtained sample was a clear colorless solution, and had an average particle size of 15 nm with a size distribution between 10 nm and 20 nm.

Example 3

The Release Profiles of VCR Encapsulated PEG2000-DSPE Micelles

Method: 0.5 ml VCR-PEG2000-DSPE micelles (1 mg/ml) was placed into 40 ml release medium (phosphate buffer physiological saline) in a dialysis bag (12-14 kD) and shaken at a constant temperature of 37° C. (100 rpm). Samples were taken at predetermined intervals and the content of VCR in the release medium was measured by HPLC. The released VCR form the micelles was calculated and the release profiles were shown in FIG. 1.

The release property of the samples in two media (phosphate buffer, pH 5.0 and pH 7.4, respectively) were studied and the results indicated that VCR was slowly released (48 hours, the release percentage was below 70%) and no burst release was observed.

Example 4

The Stability of VCR-PEG2000-DSPE Micelles 1 ml VCR-PEG2000-DSPE micelle (1 mg/ml) prepared as above was placed into a 250 ml flask and 100 ml phosphate buffer, pH 7.4 was added. After incubating in 37° C. water bath for 2 hours, 300 μl sample was placed into a filter tube (molecular sieve: 30 kD) and subjected to centrifugation at 10,000 rpm for 10 minutes. The content of VCR in the filtrate was determined by HPLC and the encapsulation efficiency of the micelle was calculated. The micelle was placed at 4° C. for 30 days and the contents of the total VCR and the free VCR were measured respectively, and the stability was investigated. The results were shown in Table 3.

TABLE 3

The stability of the VCR-PEG2000-DSPE micelle

| Lipids/Medicament (1:5, mol/mol), VCR (1 mg/ml) | Content (%) | Encapsulation efficiency (%) |
| --- | --- | --- |
| 0 day | 100 | 99.4 |
| Encapsulation efficiency before dilution | | 99.4 |
| Encapsulation efficiency after dilution (100 fold) | | 98.5 |
| 30 days | 98.6 | 99.4 |

Example 5

In vitro Cytotoxicity Assay of VCR Encapsulated PEG2000-DSPE Micelles

A cytotoxicity assay in vitro was used to verify the antitumor effect of the nano-micellar preparation containing vincristine according to present invention.

Figure 2:
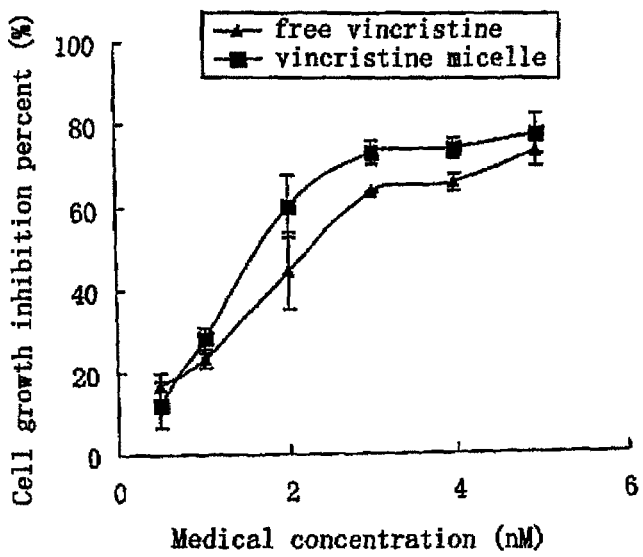
FIG. 2 illustrates the in vitro cytotoxicity assay of VCR encapsulated PEG2000-DSPE micelles.

MCF-7 cells (Human breast cancer cell line, ATCC, HTB-22) were inoculated on a 96-well plate ($3.0 \times 10^3$/well) and incubated overnight. Culture media was then washed out and 10 μl samples with various concentrations of vincristine (both free vincristine and vincristine encapsulated in PEG-distearyl phosphatidylethanolamine micelle) were added in triplicate respectively. To each well was added 100 μl medium supplemented with 10% fetal calf serum, and the cells were grown in an incubator (37° C., 5% $CO_2$) for further 72 hours. Cells were taken out at each setting time points and added with 20 μl MTT (5 mg/ml). After incubation for further 4 hours, each well was added with 150 μl DMSO for dissolution and then placed into a Micro-Plate Reader to read out its maximum absorption at 590 nm. The growth curve was plotted for each concentration and shown in FIG. 2.

Example 6

The Encapsulation Efficiency of VNR Encapsulated PEG2000-DSPE Micelles

TABLE 4

The encapsulation efficiency of VNR encapsulated PEG2000-DSPE micelles

| Lipids/Medicament (mol/mol) | Hydrated solution | Encapsulation efficiency (%) |
| --- | --- | --- |
| 1.25:1 | Water for injection | 72.2 |
| 2.5:1 | Water for injection | 96.7 |

TABLE 4-continued

The encapsulation efficiency of VNR encapsulated PEG2000-DSPE micelles

| Lipids/Medicament (mol/mol) | Hydrated solution | Encapsulation efficiency (%) |
| --- | --- | --- |
| 4:1 | Water for injection | 99.7 |
| 5:1 | Water for injection | 99.9 |
| 6:1 | Water for injection | 100 |

Preparation process: According to Lipids/Medicament ratios in above formulation, VNR was weighed and dissolved in chloroform (2 mg/ml). PEG2000-DSPE was weighed and dissolved in a suitable amount of chloroform, and then placed into a 100 ml leptoclados-type bottle. The organic solvent was removed completely using a rotary evaporator to form a thin uniform phosphatide film on the surface of the leptoclados-type bottle. Water for injection was added to the leptoclados-type bottle and hydration was performed by shaking at 50° C. for 1 hour under the protection of nitrogen atmosphere. 0.22 μm microfiltration membrane was used for filtration sterilization to produce the micellar preparation containing vinorelbine for intravenous injection. The obtained sample was a clear colorless solution, and had an average particle size of 15 nm with a size distribution between 10 nm and 20 nm.

Example 7

Figure 3:
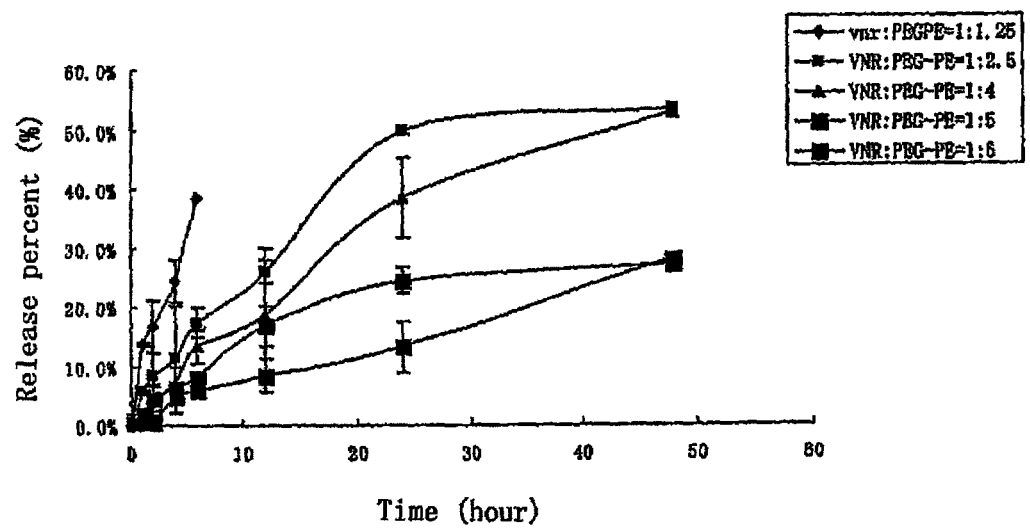
FIG. 3 illustrates the release profiles of VNR encapsulated PEG2000-DSPE micelles at different ratios of Lipids/Medicament.

The Release Profiles of VNR Containing PEG2000-DSPE Micelles at Different Ratios of Lipids/Medicament Method: 0.5 ml VNR-PEG2000-DSPE micelles (3 mg/ml) formed with different ratios of lipids/medicament were placed into 40 ml release medium (phosphate buffer physiological saline) in a dialysis bag (12-14 kD) and shaken at a constant temperature of 37° C. (100 rpm), respectively. Samples were taken at predetermined intervals and the content of VNR in the release medium was measured by HPLC. The released VNR from the micelles was calculated and the release profiles were shown in FIG. 3.

The release property of the samples in the medium (phosphate buffer, pH 7.4) was studied and the results indicated that VNR was slowly released (48 hours, the release percentage was below 30%) when the micelles formed at the ratio of lipids/medicament ratio (5-6:1) and no burst release was found.

Example 8

The Release Profiles of VNR Encapsulated PEG2000-DSPE Micelles in the Different Batches Method: 0.5 ml VNR-PEG2000-DSPE micelles (3 mg/1 ml) formed at the ratio of lipids/medicament (5:1) in the three different batches were placed into 40 ml release medium (phosphate buffer physiological saline) in a dialysis bag (12-14 kD) and shaken at a constant temperature of 37° C. (100 rpm), respectively. Samples were taken at predetermined intervals and the content of VNR in the release medium was measured by HPLC. The released VNR from the micelles was calculated and the release profiles were shown in FIG. 4.

Figure 4:
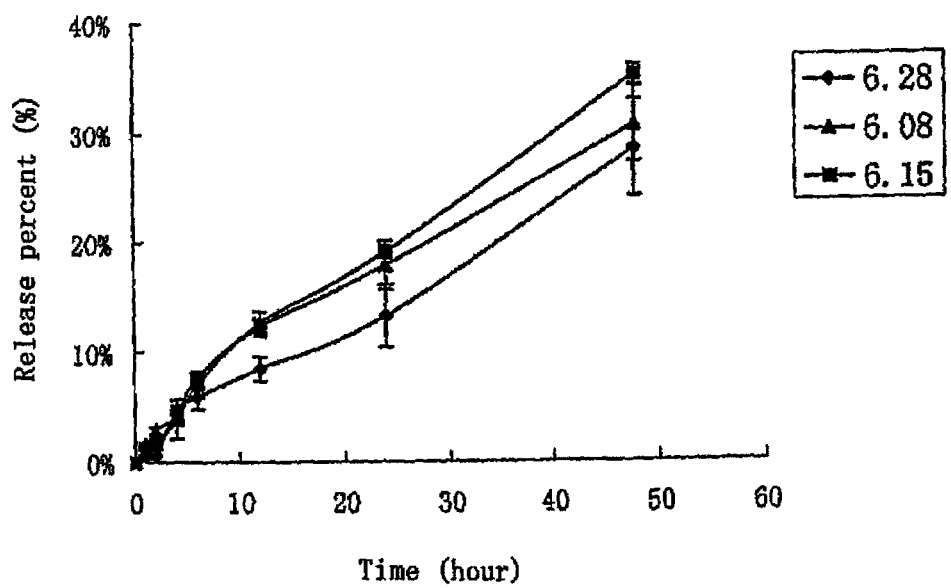
FIG. 4 illustrates the release profiles of VNR encapsulated PEG2000-DSPE micelles in the different batches.

As shown in FIG. 4, VNR-PEG2000-DSPE micelles in the three different batches had no significant change in terms of release property and no burst release was found. Thus, the preparation process of the micelles was stable.

Example 9

The Stability of VNR Encapsulated PEG2000-DSPE Micelles 1 ml VNR-PEG2000-DSPE micelle (3 mg/1 ml) was placed into a 250 ml flask and 100 ml phosphate buffer, pH 7.0 was added. After incubating in 37° C. water bath for 2 hours, 300 μl sample was placed into a filter tube (molecular sieve: 30 kD) and subjected to a centrifugation at 10,000 rpm for 10 minutes. The content of VNR in the filtrate was determined by HPLC and the encapsulation efficiency of the micelle was calculated. The micelle was placed at 4° C. for 30 days and the contents of the total VNR and the free VNR were measured, respectively, and the stability was observed. The results were shown in Table 5.

TABLE 5

The stability of the VNR-PEG2000-DSPE micelle

| Lipids/Medicament (5:1, mol/mol), VNR (1 mg/ml) | Content (%) | Encapsulation efficiency (%) |
| --- | --- | --- |
| 0 day | 100 | 99.9 |
| Encapsulation efficiency before dilution | | 99.9 |
| Encapsulation efficiency after dilution (100 fold) | | 99.4 |
| 30 days | 98.6 | 99.4 |

Example 10

Tumor Growth Inhibition Assay in vivo of Vinorelbine Micellar Preparation

Figure 5:
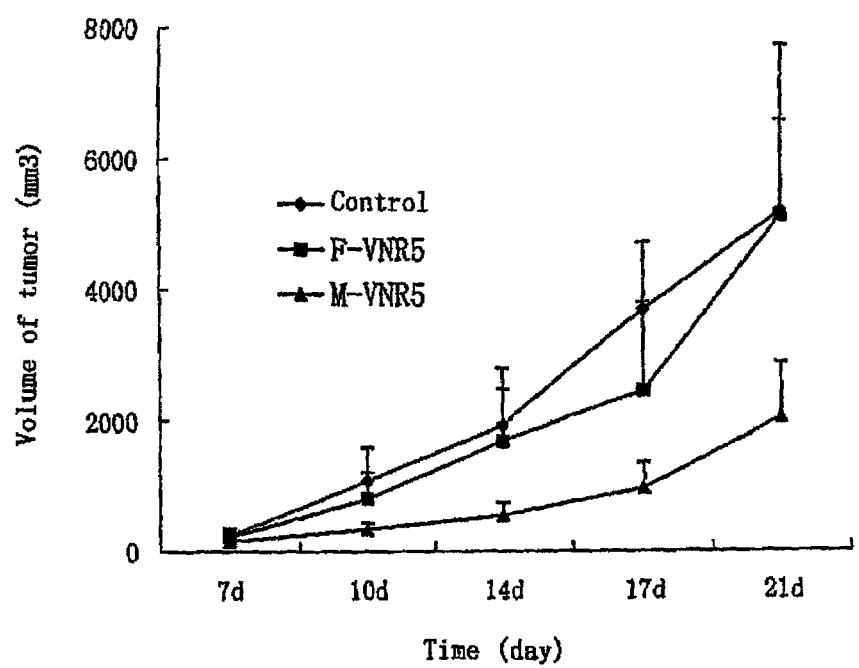
FIG. 5 illustrates the effect of F-VNR and M-VNR on the inhibition of tumor growth in mice.

Fresh Lewis lung cancer cells (ATTC, CRL-1642) were inoculated subcutaneously into the axillary region of right forelimb of Balb/c mice (1×10$^7$/ml, 0.2 ml/mice). The mice (17-19 g, female) bearing tumor were then randomly divided into three groups, i.e. control group, free vinorelbine group (F-VNR) and vinorelbine micelle group (M-VNR), 6 mice each group. Administration was carried out on the next day to the inoculation. The doses of both F-VNR and M-VNR were 5 mg/kg (drug concentration: 0.5 mg/ml), iv volume 0.1 ml/10 g body weight, and the dose of the control group was iv 0.1 ml/10 g body weight of physiological saline. Dosing was performed once a week and continued for three weeks (dosing on the 1$^{st}$, 8$^{th}$ and 15$^{th}$ day, respectively), wherein the length (a) and width (b) of the tumors were measured with vernier caliper on the 7$^{th}$, 10$^{th}$, 14$^{th}$, 17$^{th}$, and 21$^{th}$ day, respectively. The volume of the tumor was calculated according the formula V=a×b$^2$/2. The results indicated that F-VNR was almost ineffective on Lewis lung cancer, while M-VNR inhibited the growth of tumor significantly at different measure time points, the inhibition percentages being within 65-70%. The experiment results were shown in FIG. 5 as well as following table.

| Group | Dose (mg/kg) | Volume of tumor (mm$^3$) | | | | |
| --- | --- | --- | --- | --- | --- | --- |
| | | 7 days | 10 days | 14 days | 17 days | 21 days |
| Control | — | 237.5 ± 116.8 | 1085.5 ± 518 | 1933.7 ± 872.7 | 3714.5 ± 1031.4 | 5228.3 ± 1402.3 |
| F-VNR | 5 | 217 ± 94.5 | 810.3 ± 407.6 | 1694.3 ± 789.1 | 2460.1 ± 1367.1 | 5163 ± 2623.8 |
| M-VNR | 5 | 154.7 ± 29.1 | 342 ± 89 | 551 ± 204.2 | 977.7 ± 395.3 | 2054.4 ± 848.5 |

What is claimed is:

1. A nano-micellar preparation for intravenous injection, comprising vinorelbine (VNR), distearyl phosphatidylethanolamine derivatized with polyethylene glycol 2000 (PEG$_{2000}$-DSPE) and a pharmaceutically acceptable adjuvant, wherein the molar ratio of the VNR to the PEG$_{2000}$-DSPE is ranged from 1:4 to 1:6, and wherein the nano-micellar preparation is a lyophilized form.

2. The micellar preparation of claim 1, wherein the pharmaceutically acceptable adjuvant is a pharmaceutically acceptable antioxidant, osmotic pressure adjusting agent, or pH adjusting agent.

3. The micellar preparation of claim 2, wherein the pH adjusting agent is citric acid-sodium citrate, acetic acid-sodium acetate, or phosphate, or the combination thereof.

4. A method of producing the nano-micellar preparation for intravenous injection according to claim 1, comprising:
   (1) dissolving the VNR and the PEG$_{2000}$-DSPE in an organic solvent;
   (2) removing the organic solvent so as to obtain a polymer lipid film containing the VNR;
   (3) adding water or a buffer solution to the polymer lipid film obtained in step (2) and hydrating, so as to obtain the nanomicelle of PEG2000-DSPE, the VNR being encapsulated therein; and
   (4) lyophilizing the obtained micelle to produce a lyophilized preparation.

5. The method of claim 4, wherein encapsulation efficiency of the VNR in the micelle is at least 90%.

6. The method of claim 4, wherein the method is further characterized by one of the following:
   the organic solvent in step (1) is methanol, ethanol, chloroform, DMSO or the mixtures thereof;
   the organic solvent is removed under reduced pressure and/or under vacuum condition in step (2);

the buffer solution in step (3) is citrate or phosphate buffer solution; and the hydrating in step (3) is performed in a water bath at a temperature between 25° C. and 70° C. for 0.5 to 2 hours.

7. The method of claim 4, further comprising: adjusting the pH of the obtained micelle solution to 3.0-8.0 with a pH adjusting agent.

8. The method of claim 6, wherein the hydrating step (3) is performed in a water bath at a temperature between 50° C. and 65° C.

* * * * *